(12) United States Patent
Gregory et al.

(10) Patent No.: US 7,132,441 B2
(45) Date of Patent: Nov. 7, 2006

(54) IMMUNOSUPPRESSIVE EFFECTS OF ADMINISTRATION OF A CYCLOOXYGENASE-2 INHIBITOR AND A 5-LIPOXYGENASE INHIBITOR

(75) Inventors: Susan A. Gregory, St. Louis, MO (US); Peter C. Isakson, Clarkson Valley, MO (US); Gary Anderson, Maryland Heights, MO (US)

(73) Assignee: G.D. Searle & Co., St. Louis, MO (US)

( * ) Notice: Subject to any disclaimer, the term of this patent is extended or adjusted under 35 U.S.C. 154(b) by 509 days.

(21) Appl. No.: 10/098,644

(22) Filed: Mar. 15, 2002

(65) Prior Publication Data

US 2002/0143033 A1    Oct. 3, 2002

Related U.S. Application Data

(60) Division of application No. 09/430,072, filed on Oct. 18, 1999, now Pat. No. 6,376,528, which is a continuation of application No. 09/189,463, filed on Nov. 10, 1998, now abandoned, which is a continuation of application No. 08/600,622, filed on Feb. 13, 1996, now abandoned.

(51) Int. Cl.
*A61K 31/415* (2006.01)
*A61K 31/34* (2006.01)

(52) U.S. Cl. ................................ 514/406; 514/471

(58) Field of Classification Search .............. 514/406, 514/471
See application file for complete search history.

(56) References Cited

U.S. PATENT DOCUMENTS

| | | | |
|---|---|---|---|
| 4,686,231 A | | 8/1987 | Bender et al. |
| 4,889,935 A | | 12/1989 | Musser |
| 5,272,178 A | | 12/1993 | Mueller et al. |
| 5,403,857 A | | 4/1995 | Edwards et al. |
| 5,859,257 A | * | 1/1999 | Talley ........................ 548/247 |
| 5,919,776 A | * | 7/1999 | Hagmann et al. ........... 514/159 |
| 5,990,148 A | * | 11/1999 | Isakson et al. .............. 514/406 |
| 6,013,644 A | * | 1/2000 | Mills et al. ............. 514/210.16 |
| 6,136,839 A | * | 10/2000 | Isakson ...................... 514/106 |
| 6,407,140 B1 | * | 6/2002 | Gregory ..................... 514/567 |
| 6,500,844 B1 | * | 12/2002 | Finke et al. ................ 514/317 |

FOREIGN PATENT DOCUMENTS

| | | |
|---|---|---|
| WO | WO 96/38418 | 12/1996 |
| WO | WO 96/38442 | 12/1996 |
| WO | WO 96/41626 | * 12/1996 |
| WO | WO 97/29776 | 8/1997 |

OTHER PUBLICATIONS

Engelhardt, CA 125:292089, abstract of Br J Rheumatol, 1996, 35 (Suppl 1), 4-12.*
Print out of Registry No. 79217-60-0 and 59865-13-3, 2003.☐☐.*
Fung-Leung, CA 123:306186, 1995.*
Potier et al., "Comparative Study of Cyclosporin A, Cyclosporin G, and the novel Cyclosporin Derivatives IMM 125 in Isolated Glomeruli and Cultured Rat Mesangial Cells: a Morphometric Analysis." Nephrol Dial Transplant, 1998, pp. 1406-1411, vol. 13.
Carter et al., 5-Lipoxygenase Inhibitory Activity of Zileuton$_1$, *J. Pharm. and Exp. Ther.*, 1991, pp. 929-937, vol. 256, No. 3, American Society for Pharmacology and Experimental Therapeutics, 1991.
Chang et al., Prevention of ocular inflammation by matrine, prednisolone, and cyclooxygenase and lipoxygenase inhibitors, *Acta Pharmacologica Sinica*, Mar. 1991, pp. 121-125, vol. 12, No. 2.
Rubin et al., Pharmacokinetics, safety, and ability to diminish leukotriene synthesis by zileuton, an inhibitor of 5-lipoxygenae, *Prog. in Inflam. Res. and Therapy*, 1991, pp. 103-116.
Tennant et al., Effects of a 5-lipoxygenase inhibitor, REV-5901, on leukotriene and histamine release from human lung tissue in-vitro, *J. Pharmacy and Pharmacology*, Apr. 1987, pp. 309-311, vol. 39, No. 4.

* cited by examiner

*Primary Examiner*—D. Margaret Seaman
(74) *Attorney, Agent, or Firm*—Philip B. Polster, II

(57) ABSTRACT

This invention is in the field of a combination comprising a therapeutically-effective amount of a cyclooxygenase-2 inhibitor, a 5-lipoxygenase inhibitor and an immunosuppressive drug selected from antiproliferative agents, antiinflammatory-acting compounds and inhibitors of leukocyte activation. This combination may be used, for example, to suppress the immune response associated with organ transplantation, graft versus host disease, and conditions with underlying autoimmune or inflammatory reactivities or responses.

18 Claims, No Drawings

IMMUNOSUPPRESSIVE EFFECTS OF ADMINISTRATION OF A CYCLOOXYGENASE-2 INHIBITOR AND A 5-LIPOXYGENASE INHIBITOR

This application is a divisional patent application of U.S. patent application Ser. No. 09/430,072 (filed Oct. 18, 1999), now U.S Pat. No. 6,376,528 which is a continuing patent application of U.S. patent application Ser. No. 09/189,463 (filed Nov. 10, 1998), now abandoned, which is a continuation of prior U.S. patent application Ser. No 08/600,622 (filed Feb. 13, 1996), now abandoned.

FIELD OF THE INVENTION

This invention is in the field of clinical immunology and relates to compositions having immunosuppressive properties. Of particular interest is a method of reducing recipient acute or chronic rejection of transplanted cells or organs, and for treatment of autoimmune diseases, hypersensitivity reactions of the acute or delayed type, allergic disorders, granulomas, meningitis, and septic shock by administering a cyclooxygenase-2 inhibitor and a 5-lipoxygenase inhibitor.

BACKGROUND OF THE INVENTION

Successful organ transplantation requires effective physiological and pharmacological intervention of the immune system of an organ recipient. Immunologic mechanisms are universal within the human species, but histocompatibility variations between organ donor and recipient may lead to rejection of donor tissue by stimulation of the recipient's immune system, except perhaps, in donor-recipient pairing of the monozygotic type. One approach to intervention of immune response in an organ transplant recipient, especially a recipient targeted for an allogenic graft, is by the use of immunosuppressive drugs. These drugs are used to prolong survival of transplanted organs in recipients in cases involving, for example, transplants of kidney, liver, hear, lung, bone marrow and pancreas.

There are several types of immunosuppressive drugs available for use in reducing organ rejection in transplantation. Such drugs fall within three major classes, namely: antiproliferative agents, antiinflammatory-acting compounds and inhibitors of lymphocyte activation.

Examples of the class of cytotoxic or antiproliferative agents are azathioprine, cyclophosphamide and methotrexate. The compound azathioprine acts by interrupting DNA synthesis through inhibition of purine metabolism. The compound cyclophosphamide is an alkylating agent which interferes with enzyme actions and cell proliferation and interrupts DNA synthesis by binding to cellular DNA, RNA, and proteins. The compound methotrexate is a folic acid antagonist which interferes with nucleotide and protein synthesis. Drugs of the antiproliferative class may be effective immunosuppressive in patients with chronic inflammatory disorders and in organ transplant recipients by limiting cell proliferation. These drugs which abrogate mitosis and cell division have severe cytotoxic side effects on normal cell populations which have a high turn-over rate, such as bone marrow cells and cells of the gastrointestinal (GI) track lining. Accordingly, such drugs often have severe side effects, particularly, lymphopenia, neutropenia, bone marrow depression, hemorrhagic cystitis, liver damage, increased incidence of malignancy, hair loss, GI tract disturbances, and infertility.

A second class of immunosuppressive drugs for use in transplantation is provided by compounds having antiinflammatory action. Representatives of this drug class are generally known as adrenal corticosteroids and have the advantage of not exerting globally systemic cytotoxic effects. These compounds usually act by preventing or inhibiting inflammatory responses or by reducing cytokine production, or by reducing chemotaxis, or by reducing neutrophil, macrophage or lymphocyte activation, or effector function. Typical examples of adrenal corticosteroids are prednisone and prednisolone which affect carbohydrate and protein metabolism as well as immune functions. Compounds of this class are sometimes used in combination with cytotoxic agents, such as compounds of the antiproliferative class because the corticosteroids are significantly less toxic. But the adrenal corticosteroids lack specificity of effect and can exert a broad range of metabolic, antiinflammatory and immune effects. Typical side effects of this class include increased organ-recipient infections and interference with wound haling, as well as disturbing hemodynamic balance, carbohydrate and bone metabolism and mineral regulation.

A third class of immunosuppressive drugs for use in organ transplantation is provided by compounds which are immunomodulatory and generally prevent or inhibit leukocyte activation. Such compounds usually act by blocking activated T-cell effector functions or proliferation, or by inhibiting cytokine production, or by preventing or inhibiting activation, differentiation or effector functions of platelet, granulocyte, B-cell, or macrophage actions. The cyclosporin family of compounds is the leading example of drugs in this class. Such compounds are polypeptide fungal metabolites which have been found to be very effective in suppressing helper T-cells so as to reduce both cellular and humoral responses to newly-encountered antigens. Cyclosporins alter macrophage and lymphocyte activity by reducing cytokine production or secretion and, in particular, by interfering with activation of antigen-specific CD4 cells, by preventing L-2 secretion and secretion of many T-cell products, as well as by interfering with expression of receptors for these lymphokines on various cell types. Cyclosporin A, cyclo[L-alanyl-D-alanyl-N-methyl-L-leucyl-N-methyl-L-leucyl-N-methyl-L-valyl-(3R,4R,6E)-6,7-didehydro-3-hydroxy-N,4-dimethyl-L-2-aminooctanoyl-L-2-aminobutanoyl-N-methylglycyl-N-methyl-L-leucyl-L-valyl-N-methyl-L-leucyl], in particular, has been used extensively as an immunosuppressive agent in organ transplantation. Other microbial metabolites include cyclosporins such as cyclosporin B and cyclosporin G, and another microbial product known as FK-506. Cyclosporin A suppresses humoral immunity as well as cell-mediated reactions. Cyclosporin A is indicated for organ rejection in kidney, liver, heart, pancreas, bone-marrow and heart-lung transplants. Cyclosporin A is also useful in the treatment of autoimmune and inflammatory diseases, including rheumatoid arthritis, Crohn's disease, Graves' disease, severe psoriasis, aplastic anemia, multiple-sclerosis, alopecia areata, penphigus and penohigoid, dermatomyositis, polymyositis, Behcet's disease, uveitis, pulmonary sarcocidiosis, biliary cirrhosis, myasthenia gravis and atopic dermatitis.

Cyclosporins possess several significant disadvantages. While cyclosporins have provided significant benefits in can transplantation, cyclosporins are non-specific immunosuppressive. Desirable immune reactions may be reduced against foreign antigens. Tolerated dosages do not provide complete suppression of rejection response. Thus, immunologic reactions to transplanted tissue are not totally impeded, requiring concomitant treatment with prednisone, methyl-prednisolone, and/or other immunosuppressive agents, including monoclonal antibodies such as anti-CD3 or anti-CD5/CD7. Cyclosporins can produce severe side effects in many organ recipients, and show host-variable effects on the liver, kidney, the CNS and GI tract. Significant among the adverse side effects are damage to the kidney and liver, hyperplasia of gum tissue, refractory hypertension and increased incidence of infections and malignancy.

Thus, the need remains for efficacious and selective immunosuppressive drugs in organ transplantation, especially for grafts between less-than-perfectly matched donor-recipient pairs.

Prostaglandins and leukotrienes are lipid mediators produced in a variety of inflammatory disease states. Both are products of metabolism of arachidonic acid. Cyclooxygenases (COX-1 and COX-2) are the enzymes that catalyze the conversion of arachidonic acid to prostaglandins. 5-Lipoxygenase (5-LO) catalyzes the conversion of arachidonic acid to leukotrienes. Products of both pathways have been described in association with transplant rejection in humans and animal models. Excess production of these mediators may play a role in accelerating loss of the transplant function, particularly in the kidney. However, little research has been directed at determining direct effects of eidosanoids on tissue rejection.

Dual inhibition of leukotrienes and prostaglandins produces profound anti-arthritic effects in the mouse collagen induced arthritis model and decrease the production of anti-native collagen antibodies in vivo. In order to determine if a cyclooxygenase-2 and 5-lipoxygenase (COX-2/5-LO) inhibitor combination has immunomodulatory or immunosuppressive effects, we evaluated the effects of treatment with cyclooxygenase-2 and/or 5-lipoxygenase inhibitors on survival time of skin grafts in mice.

Compounds which selectively inhibit cyclooxygenase-2 have been described. US. Pat. No. 5,380,738 describes oxazoles which selectively inhibit cyclooxygenase-2. U.S. Pat. No. 5,344,991 describes cyclopentenes which selectively inhibit cyclooxygenase-2. U.S. Pat. No. 5,393,790 describes spiro compounds which selectively inhibit cyclooxygenase-2. WO documents WO94/15932 describes thiophene and furan derivatives which selectively inhibit cyclooxygenase-2. WO94/27980 describes oxazoles which selectively inhibit cyclooxygenase-2. WO95/00501 describes compounds which selectively inhibit cyclooxygenase-2. WO94/13635 describes compounds which selectively inhibit cyclooxygenase-2. WO94/20480 describes compounds which selectively inhibit cyclooxygenase-2. WO94/26731 describes compounds which selectively inhibit cyclooxygenase-2. WO documents WO95/15316 describes pyrazolyl sulfonamide derivatives which selectively inhibit cyclooxygenase-2.

Compounds which inhibit 5-lipoxygenase have been described. U.S. Pat. No. 5,234,950 describes tetrahydrofuran derivatives. U.S. Pat. No. 5,098,932 describes cyclic ether derivatives. U.S. Pat. No. 5,354,865 describes tetrahydropyrans. U.S. Pat. Nos. 4,873,259, 5,220,059 and 5,288,751 describe hydroxureas as lipoxygenase inhibitors. Acetylene derivatives have been described as having 5-LO activity in WO92/01682.

Compounds which inhibit cyclooxygenase and 5-lipoxygenase have been described. U.S. Pat. No. 5,298,521 describes pyrazole thiocarbamates. U.S. Pat. No. 5,242,940 describes pyrazoles as inhibiting both enzymes. U.S. Pat. No. 5,356,898 describes di-tert-butylpyrimidines. however, these previous mixed inhibitors do not selectively inhibit cyclooxygenase-2 and therefore still cause the gastrointestinal side effects which substantially reduce their usage and effectiveness.

Combined therapies of NSAIDs and other reagents are known in the art. Combination analgesics have been reported (W. Beaver, *Am. J. Med.*, 77, 38 (1984)) although such combinations do not substantially reduce adverse effects. The combination of NSAIDs and steroids have been described. A combination of indomethacin, steroid and lipopolysaccharide has been reported for the treatment of spinal injure (L. Guth et al., *Proc. Natl. Acad. Scd. USA*, 91, 12308 (1994)). G. Hughes et al. describe combinations of corticosteroids with NSAIDs for the treatment of sunburn (Dermatology, 184, 54 (1992)). C. Stewart: et al. (*Clin. Pharmacol. Ther.*, 47, 540 (1990)) describe the combination of naproxen and methotrexate as safe, although concurrent administrations of methotrexate with other NSAIDs have been reported to be toxic and sometimes fatal. A combination of a dual 5-lipoxygenase/cyclooxygenase inhibitor with a glucocorticoid is described for the treatment of skin disorders (K. Tramposch, *Inflammation*, 17, 531 (1993)). Combinations of NSAIDs and steroids should be used in the treatment of scleritis only if patients are not responsive to any other treatment (S. Lightman and P. Watson, *Am. J. Ophthalmol.*, 108, 95 (1989)). Combinations of cyclooxygenase inhibitors, lipoxygenase inhibitors, collagenase inhibitors and cytotoxic agents have been used in the treatment of non-small-cell lung cancers (B. Teicher et al., *Cancer. Chemother. Pharmacol.*, 33, 515 (1994)). Combinations of naproxen with other NSAIDs have been described in the treatment of arthritis. R. Willikens and E. Segre (Arthritis Rheum., 19, 677 (1976)) describe the combination of aspirin and naproxen as being more effective than aspirin alone for the treatment of rheumatoid arthritis. Naproxen and acetaminophen together were described or treating the pain associated with arthritis (P. Seideman et al., *Acta Orthop. Scand.*, 64, 285 (1993)). However, combinations of naproxen with indomethacin or ibuprofen offer no advantage in the treatment of arthritis (M. Seifert and C. Engler, *Curr. Med. Res. Opin.*, 7, 38 (1980)).

Tenidap has been described as inhibiting cyclooxygenases and cytokine-modifying [F. Breedveld Scand. *J. Rheumatol.*, 23 (Supp. 100), 31 (1994)]. WO patent Publication 94/02448, published Feb. 3, 1994, describes hydroxamic acid derivatives as dual 5-lipoxygenase and cyclooxygenase inhibitors having immunosuppressant utility. U.S. Pat. No. 4,595,699, to Terada et al., describes phenyl alkanoic acid derivatives as having analgesic, antiinflammatory and immune regulating activity. R. Bartlett et al. describe thiazolo(3,2-b) (1,2,4)triazin-7-ones as antiinflammatory agents with immunomodulating properties [*Drugs Exptl. Clin. Res.*, 15, 521 (1989)]. J. Shaw and P. Greatorex [*Adv. Prostaglandin, Thromboxane, Leukotriene Res.*, 13, 219 (1985)] describe that whereas aspirin and sodium salicylate prolong graft survival, a cyclooxygenase inhibitor reduced the survival period. V. Fimiani, et al. describe some NSAID's that may have activity in the treatment of autoimmune diseases [*EOS-Revista di Immunologia and Immunofarmacologia*, 13, 58 (1993)]. A. Badger et al. describe an indomethacin enhancement of suppressor cell population [*Immunopharm.*, 4, 149 (1982)]. J. Shelby et al. [*Transplantation Proc.*, 19, 1435 (1987)] describe indomethacin as reversing transfusion-induced graft prolongation. D. Latter et al. indicate that indomethacin was effective as an immunomodulator following burns [*J. Surg. Res.*, 43, 246 (1987)]. J. Tarayre et al. describe indomethacin as having an effect in their delayed hypersensitivity models [*Arzneim. -Forsch./Drug Res.*, 40, 1125 (1990)]. D. Braun et al indicate that a prostaglandin synthetase inhibitor may help prevent chemotherapy-induced decline in immune reactivity (*Proc. An. Soc. Clin. Oncol.*, 4, 21 Meeting, 223 (1985)]. Administration of tepoxalin (dual 5-LO and COX inhibitor) and cyclosporine has been described [Fung-Leung, et al., *Transplantation*, 60, 362 (1995)] in suppression of graft versus host reaction although the effect of tepoxalin did not appear to be related to the inhibition of arachidonic acid metabolism.

There have been no reported combinations of a cyclooxygenase-2 selective inhibitor and a 5-lipoxygenase inhibitor as having a significant prolongation of graft survival.

DESCRIPTION OF THE INVENTION

Reduction in recipient rejection of a transplanted organ, or treatment of an autoimmune or inflammatory disease, or a hypersensitivity reaction of the acute or delayed type, an allergic reaction or asthmatic disorder, or treatment of dermatitis, arthritis, meningitis, granulomas, vasculitis, septic shock or graft vs. host response may be accomplished by a method to prevent or suppress immune responses in a recipient or treatment subject, which method comprises treating the subject with a therapeutically-effective amount of an immunosuppressive combination of a cyclooxygenase-2 inhibitor and a 5-lipoxygenase inhibitor.

The specification and claims of this invention include trademarked names and trade named compounds. The table below identifies and defines each trademark or trade name by its associated chemical name.

| Trademark | Chemical Name |
| --- | --- |
| Abbott A-65260 | tetrahydro-1-phenyl-1,2,4-triazin-3(2H)-one |
| Abbott A-69412 | N-[1-(3-Furyl)ethyl]-N-hydroxyurea |
| Abbott A-76745 | N-Hydroxy-N-[4-[3-(4-fluorophenoxy)phenyl]-3-butyn-2-yl]-urea |
| Abbott A-78773 | N-[[5-(4-fluorophenoxy)furan-2-yl]-1-methyl-2-propynyl]-N-hydroxyurea |
| Abbott A-79175 | N-[3-[5-(4-fluorophenoxy)-2-furanyl]-1-methyl-2-propynyl]-N-hydroxyurea |
| Abbott A-121798 | 1-methyl-6-[[[3-(tetrahydro-4-methoxy-2-methyl-2H-pyran-4-yl)-2-propenyl]oxy]methyl]-2(1H)-quinolinone |
| Abbott ABT 761 | (R)-(+)-N-[3-[5-[(4-fluorophenyl)methyl]-2-thienyl]-1-methyl-2-propynyl]-N-hydroxyurea |
| Abbott-63162 | N-hydroxy-N-[1-[4-(phenylmethoxy)phenyl]ethyl]-acetamide |
| American Home Products WAY-121520 | 1-[(4-chlorophenyl)methyl]-2-methyl-5-(2-quinolinylmethoxy)-1H-indole-3-acetic acid |
| American Home Products Wy-48252 | 1,1,1-trifluoro-N-[3-(2-quinolinylmethoxy)phenyl]-methanesulfonamide |
| American Home Products Wy-50295 | α-methyl-6-(2-quinolinylmethoxy)-2-naphthalene-acetic acid |
| American Home Products WAY-120739 | 1,8-diethyl-1,3,4,9-tetrahydro-6-(2-quinolinylmethoxy)-pyrano[3,4-b]indole-1-acetic acid |
| American Home Products AHR-5333 | 1-[4-[3-[4-[bis(4-fluorophenyl)hydroxymethyl]-1-piperidinyl]propoxy]-3-methoxyphenyl]-ethanone |
| American Home Products WY 47288 | 2-[(1-naphthalenyloxy)methyl]-quinoline |
| Bayer Bay-x-1005 | (R)-2-[4-(quinolin-2-yl-methoxy)phenyl]-2-cyclopentyl-acetic acid |
| Biofor BF-389 | dihydro-4-(3,5-di-tert-butyl-4-hydroxybenzylidene)-2-methyl-2H-1,2-oxazin-3(4H)-one |
| Boehringer Ingelheim BI-L-93BS | 2,6-bis(1,1-dimethylethyl)-4-[2-(3-pyridinyl)ethenyl]-phenol |
| Boehringer Ingelheim BI-L-357 | mono[2,6-dimethyl-4-[(1E)-2-(2-thienyl)ethenyl]phenyl]-butanedioic acid |
| Boehringer Ingelheim BIL 226XX | 2,6-dimethyl-4-[2-(2-thienyl)ethenyl]-phenol |
| Bristol Myers Squibb BU-4601A | 2-amino-5-hydroxy-8-methylnonyl ester-benzoic acid |
| Bristol-Myers Squibb BMY-30094 | 9-phenylnonanophydroxamic acid |
| bunaprolast | 2-butyl-4-methoxy-1-naphthalenol-acetate |
| carbazomycin C | 3,6-dimethoxy-1,2-dimethyl-9H-carbazol-4-ol |
| carbazomycin B | 4-hydroxy-3-methoxy-1,2-dimethylcarbazole |
| Chauvin CBS-1114 | 2-phenylhydrazide-benzenecarboximidic acid |
| Chiesi CHF-1909 | monohydrobromide-6-(2,2-dimethylhydrazino)-5,6,7,8-tetrahydro-1,2-naphthalenediol |

-continued

| Trademark | Chemical Name |
|---|---|
| Ciba-Geigy CGS-26529 | N-[2-[[2-[(4'-fluoro[1,1'-biphenyl]-4-yl)methyl]-1,2,3,4-tetrahydro-1-oxo-6-isoquinolinyl]oxy]ethyl]-N-hydroxy-urea |
| Ciba-Geigy CGS 24891 | N-[[6-(4-fluorophenoxy)-2H-1-benzopyran-3-yl]methyl]-N-hydroxy-N-methyl-urea |
| Ciba-Geigy CGS-23885 | N-hydroxy-N-[(6-phenoxy-2H-1-benzopyran-3-yl)methyl]-urea |
| Ciba-Geigy CGS 22745 | (2E)-3-[4-(2,5-dimethyl-1H-pyrrol-1-yl)phenyl]-N-hydroxy-N-methyl-2-propenamide |
| Ciba-Geigy CGS-21595 | 4-(cyclohexyl methylamino)-1,2-naphthalenediol, diacetate ester |
| Ciba-Geigy CGS-8515 | methyl 2-[(3,4-dihydro-3,4-dioxo-1-naphthalenyl)amino]-benzoate |
| cirsiliol | 3',4',5-trihydroxy-6,7-dimethoxyflavone |
| Cytomed CMI-392 | N'-[[2-[2-[(4-chlorophenyl)thio]ethoxy]-3-methoxy-5-[(2R,5R)-tetrahydro-5-(3,4,5-trimethoxyphenyl)-2-furanyl]phenyl]methyl]-N-hydroxy-N-methyl-urea |
| Dainippon AL-3264 | N-[4-[4-(diphenylmethyl)-1-piperazinyl]butyl]-3-(6-methyl-3-pyridyl)acrylamide |
| docebenone | 3,5,6-trimethyl-1,4-dione-2-(12-hydroxy-5,10-dodecadiynyl)-2,5-cyclohexadiene |
| DuPont Merck DuP-654 | 2-benzyl-1-naphthol |
| DuPont Dup 697 | 5-bromo-2-(4-fluorophenyl)-3-[4-(methylsulfonyl)phenyl]-thiophene |
| Eisai E 3040 | 6-hydroxy-5,7-dimethyl-2-methylamino-4-(3-pyridylmethyl)-benzothiazole |
| Eisai E-6080 | 6-hydroxy-2-(4-sulfamoylbenzylamino)-4,5,7-trimethylbenzothiazole hydrochloride |
| Eisai E 5110 | N-methoxy-3-(3,5-di-tert-butyl-4-hydroxybenzylidene pyrrolidin-2-one |
| enazadrem phosphate | 4,6-dimethyl-2-[(6-phenyl hexyl)amino]-5-pyrimidinol phosphate (1:1) (salt) |
| enofelast | 4-[(1E)-2-(4-fluorophenyl)ethenyl]-2,6-dimethyl-phenol |
| Epocarbazolin-A | 1,6-diol, 4-(hydroxymethyl)-7-methyl-8-[3-methyl-3-(3-methylbutyl)oxiranyl]-9H-carbazole |
| Eprovafen | 5-(3-phenylpropyl)-2-thiophenepentanoic acid |
| Evandamine | 4,5-dihydro-5-methyl-1-(4,5,6,7-tetrahydro-2-benzothiazolyl)-1H-pyrazol-3-amine |
| Fisons FPL 62064 | N-(4-methoxyphenyl)-1-phenyl-1H-pyrazol-3-amine |
| FK-506 | (3S,4R,5S,8R,9E,12S,14S,15R,16S,18R,19R,26aS)-1,7,20,21(4H,23H)-tetrone, 5,6,8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methylethenyl]-14,16-dimethoxy-4,10,12,18-tetramethyl-8-(2-propenyl)-15,19-epoxy-3H-pyrido[2,1-c][1,4]-oxaazacyclotricosine |
| flezelastine hydrochloride | 4-[(4-fluorophenyl)methyl]-2-[hexahydro-1-(2-phenylethyl)-1H-azepin-4-yl]-1(2H)-phthalazinone |
| flobufen | 4-[2',4'-difluorbiphenyl]-4-oxo-methyl-butanic acid |
| flosulide | N-[6-(2,4-difluorophenoxy)-2,3-dihydro-1-oxo-1H-inden-5-yl]-methanesulfonamide |
| Forsythiaside | 4-[(2E)-3-(3,4-dihydroxyphenyl)-2-propenoate[-2-(3,4-dihydroxy phenyl)ethyl-6-O-(6-deoxy-a-L-mannopyranosyl)-b-D-Glucopyranoside |
| Fujirebio F-1322 | N-[2-(4-(benzhydryloxy)piperidino)ethyl]-3-hydroxy-5-(3-pyridylmethoxy)-2-naphthamide |
| Fujisawa FR 110302 | 2,2-dibutyl-1,2,3,4-tetrahydro-5-(2-quinolinylmethoxy)-1-naphthalenol |
| Kyowa Hakko KF-8940 | 2-n-heptyl-4-hydroxyquinoline-N-oxide |
| lagunamycin | 6-diazo-3-methyl-4-[(1E)-1,3,5-trimethyl-1-hexenyl]-2,5,7,8(1H,6H)-quinolinetetrone |
| Leo Denmark ETH-615 | 4-(2-quinolylmethoxy)-N-(3-fluorobenzyl-phenyl-amino-methyl-4-benzoic-acid |
| Lilly LY-269415 | 5-[[3,5-bis(1,1-dimethylethyl)-4-hydroxy phenyl]methylene]-3-(methylamino)-4-thiazolidinone |
| Lilly LY 178002 | 5-[[3,5-bis(1,1-dimethyl ethyl)-4-hydroxyphenyl]methylene]-4-thiazolidinone |
| Lilly LY-233569 | N-hydroxy-N-methyl-3-[2-(methylthio)phenyl]-2-propenamide |
| Linazolast (TMK-688) | 1-([5-(3-methoxy-4-ethoxycarbonyloxyphenyl)-2,4-pentadienoyl]aminoethyl)-4-diphenylmethoxypiperidine |
| lonapalene | 6-chloro-2,3-dimethoxynaphthalene-1,4-diol-diacetate |

-continued

| Trademark | Chemical Name |
|---|---|
| masoprocol | (R*,S*)-4,4-(2,3-dimethyl-1,4-butanediyl)bis-1,2-benzenediol |
| meloxicam | 1,1-dioxide-4-hydroxy-2-methyl-N-(5-methyl-2-thiazolyl)-2H-1,2-benzothiazine-3-carboxamide |
| Merck Frosst L 739010 | 1,6-anhydro-3-C-[6-[[[7-cyano-5-(3-furanyl)-2-naphthal enyl]oxy]methyl]-2-pyridinyl]-2,4-dideoxy-b-D-threo-hexopyranose |
| Merck Frosst L 663536 | 3-[1-(4-chlorobenzyl)-3-t-butyl-thio-5-isopropylindol-2-yl]-2,2-dimethylpropanoic acid |
| Merck & Co MK-866 | 3-[1-(4-chlorobenzyl)-3-t-butyl-thio-5-isopropylindol-2-yl]-2,2-dimethylpropanoic acid |
| Merck Frosst L 699333 | (2-[2-[1-(4-chlorobenzyl)-4-methyl-6-[(5-phenylpyridin-2-yl)methoxy]-4,5-dihydro-1H-thiopyrano[2,3,4-cd]indol-2-yl]ethoxy]-butanoic acid |
| Merck & Co L-656224 | 2-[(4-methoxyphenyl)methyl]-3-methyl-4-hydroxy-5-propyl-7-chlorobenzofuran |
| Merck & Co L-651896 | 6-[1-[2-(hydroxymethyl)phenyl]-1-propen-3-yl]-2,3-dihydro-5-benzofuranol |
| Merck & Co L-651392 | 4-bromo-2,7-dimethoxy-3,4-phenothizin-3-one |
| Merck & Co L-670630 | 2,3-dihydro-6-(3-phenoxypropyl)-2-(2-phenylethyl)-5-benzofuranol |
| Merck & Co L-674636 | [[4-(4-chlorophenyl)-1-[4-(2-quinolinylmethoxy)phenyl]butyl]thio]-acetic acid |
| Merck & Co L-652343 | 3-hydroxy-5-trifluoromethyl-N-(2-(2-thienyl)-2-phenyl-ethenyl)-benzo(b)thiophene-2-carboxamide |
| Merck & Co MK-591 | 3-(1((4-chlorophenyl)methyl)-3((1,1-dimethyl-ethyl)thio)-5(quinolin-2-yl-methyl-oxy)-1H-indol-2-yl)-2,2-dimethyl-propanoate |
| Merckle ML-3000 | [2,2-dimethyl-6-(4-chlorophenyl)-7-phenyl-2,3-dihydro-1H-pyrrolizine-5-yl]-acetic acid |
| Nippon NKT-01 | trihydrochloride-7-[(aminoiminomethyl)amino]-N-[2-[[4-[(3-aminopropyl)amino]butyl]amino]-1-hydroxy-2-oxoethyl]-heptanamide |
| nitrosoxacin-A | N-hydroxy-14-methyl-N-nitroso-1-pentadecanamine |
| Ono ONO-LP-219 | (23,11Z,14Z)-N-[2,3-dihydro-3-(1H-tetrazol-5-yl)-1,4-benzodioxin-5-yl]-N-methyl-2,11,14-eicosatrienamide |
| Ono ONO-LP-269 | (2E,11Z,14Z)-N-[4-hydroxy-2-(1H-tetrazol-5-yl)-8-quinolinyl]-2,11,14-eicosatrienamide |
| Ono ONO-5349 | 2-amino-4-[(4-methylphenyl)thio]-phenol hydrochloride |
| Purdue-Frederick PF-5901 | 2-[3(1-hydroxyhexyl)phenoxymethyl]-quinoline hydrochloride |
| Rhone-Poulenc Rorer Rev-5367 | methyl-2-[[3-(1-hydroxypentyl) phenoxy]methyl]-benzoic acid (ester) |
| Rhone-Poulenc Rorer RG-5901-A | a-pentyl-3-(2-quinolinylmethoxy)-benzenemethanol |
| Rhone-Poulenc Rorer RG-6866 | N-hydroxy-N-methyl-4-(phenylmethoxy)-benzeneacetamide |
| rilopirox | 6-[[4-(4-chlorophenoxy)phenoxy]methyl]-1-hydroxy-4-methyl-2(1H)-pyridinone |
| Sandoz QA-208-199 | N-hydroxy-N-methyl-7-propoxy-2-naphthaleneethanamine |
| Schering Plough SCH 40120 | 10-(3-chlorophenyl)-6,8,9,10-tetrahydro-benzo[b][1,8]naphthyridin-5(7H)-one |
| Searle SC-41661A | 3-(3,5-bis(1,1-dimethyl)-4-hydroxyphenyl)thiol]-N-methyl-N-[2-(2-pyridinyl-propanamide) |
| Searle SC-45662 | (R*,S*)-1-methylpropoxy]-[(1R,2S)-2-[[3,5-bis(1,1-dimethylethyl)-4-hydroxyphenyl]thio]-acetic acid |
| SmithKline Beecham SK&F-104351 | 2-(4-fluorophenyl)-6,7-dihydro-3-(4-pyridinyl)-5H-pyrrolo[1,2-a]-imidazole |
| SmithKline Beecham SK&F-104493 | 6,7-dihydro-2-(4-methoxyphenyl)-3-(4-pyridinyl)-5H-pyrrolo[1,2-a]-imidazole |
| SmithKline Beecham SK&F-105809 | 2-(4-methylsulfinylphenyl)-3-(4-pyridyl)-6,7-dihydro-[5H]-pyrrolo[1,2-a]-imidazole |
| SmithKline Beecham SB-202235 | (S)-N-hydroxy-N-(2,3-dihydro-6-phenylmethoxy-3-benzyofuranyl)-urea |
| Syntex RS-61443 | (4E)-6-(1,3-dihydro-4-hydroxy-6-methoxy-7-methyl-3-oxo-5-isobenzofuranyl)-4-methyl-,2-(4-morpholinyl)ethyl ester,4-hexenoic acid |
| tagorizine | (2E)-N-[4-[4-(diphenylmethyl)-1-piperazinyl]butyl]-3-(6-methyl-3-pyridinyl)-2-propenamide |
| Taisho NS-398 | N-[2-(cyclohexyloxy)-4-nitrophenyl]-methanesulfonamide |
| Takeda CV-6504 | 2,3,5-Trimethyl-6-(3-pyridylmethyl)-1,4-benzoquinone |

| Trademark | Chemical Name |
|---|---|
| Teijin TEI-8005 | (7E)-8-(2-naphthyl)-5,6-trans-5,6-methano-7-octenoic acid |
| Teiko Hormone TZI-41127 | 2-(4-hydroxy-3,5-dimethylphenyl)-5-methoxy-3-methylindole |
| tenidap | (Z)-5-Chloro-2,3-dihydro-3-(hydroxy-2-thienylmethylene)-2-oxo-1H-indole-1-carboxamide |
| tepoxalin | 5-(4-chlorophenyl)-N-hydroxy-(4-methoxyphenyl)-N-methyl-1H-pyrazole-3-propanamide |
| Terumo TMK-777 | (2E,4E)-N-[2-[4-(diphenyl methoxy)-1-piperidinyl] ethyl]-5-(4-hydroxy-3-methoxyphenyl)-2,4-pentadienamide |
| Terumo TMK-992 | (2E)-N-[2-[4-[(4-chlorophenyl)phenylmethyl]-1-piperazinyl]ethyl]-3-(4-hydroxy-3-methoxyphentyl)-2-propenamide |
| Terumo TMK-919 | (2Z,5Z,8Z,11Z,14Z,17Z)-N-[4-[[(2E)-3-(3,4-dihydroxyphenyl)-1-oxo-2-propenyl]amino]butyl]-2,5,8,11,14,17-eicosahexaenamide |
| Terumo TMK-789 | (2E)-N-[3-[4-(diphenylmethyl)-1-piperazinyl]propyl]-3-(4-hydroxy-3-methoxy phenyl)-2-propenamide |
| Terumo TMK-781 | (2E)-N-[2-[4-(diphenylmethoxy)-1-piperidinyl]ethyl]-3-(4-hydroxy-3-methoxy phenyl)-2-propenamide |
| Warner-Lambert PD-127443 | (E)-2,6-bis(1,1-dimethyl-ethyl)-4-[2-(5-methyl-1H-pyrazol-3-yl)ethenyl]-phenol |
| Warner-Lambert PD-145246 | 4-[4,6-bis-t-butyl-5-hydroxy-2-pyrimidinyl]-1,3-dihydro-5-methyl-2H-imidazol-2-one |
| Warner-Lambert CI 1004 | (Z)-5-[[3,5-bis(1,1-dimethylethyl)-4-hydroxyphenyl]-methylene]-2-imino-4-thiazolidinone-methanesulfonate salt |
| Warner-Lambert CI-986 | 5-[3,5-bis(1,1-dimethylethyl)-4-hydroxyphenyl]-1,3,4-thiadiazole-2(3H)-thione, choline salt |
| Warner-Lambert CI-987 | 5-[[3,5-bis(1,1-dimethylethyl)-4-hydroxyphenyl]methylene]-2,4-thiazolidinedione |
| Wellcome BW-B218C | N-hydroxy-N-[1-methyl-3-(3-phenoxyphenyl)-2-propenyl]-acetamide |
| Yoshitomi Y-19432 | 1-butyl-5-hydroxy-2-methyl-N-[1-(2-phenylethyl)-4-piperidinyl]-1H-indole-3-carboxamide, hydrochloride |
| Zeneca ZM 230487 | (6-[(3-fluoro-5-[4-methoxy-3,4,5,6-tetrahydro-2H-pyran-4-yl])phenoxymethyl]-1-ethyl-2-quinolone |
| Zeneca ZD-2138 | 6-[(3-fluoro-5-[4-methoxy-3,4,5,6-tetrahydro-2H-pyran-4-yl])phenoxy-methyl]-1-methyl-2-quinolone |
| Zeneca ICI-211965 | 1-[3-(naphth-2-ylmethoxy)phenyl]-1-(thiazol-2-yl)propyl methyl ether |
| Zeneca ZM-216800 | 2-[2,3-dihydro-1-methoxy-6-(2-naphthalenylmethoxy)-1H-inden-1-yl]-thiazole |
| zileuton | N-(1-Benzo[b]thien-2-yl-ethyl)-N-hydroxyurea |

In addition, the invention describes a combination comprising a therapeutically-effective amount of a 5-lipoxygenase inhibitor and a cyclooxygenase-2 inhibitor selected from Dupont Dup 697, Taisho NS-398, meloxicam, flosulide and compounds of Formula I

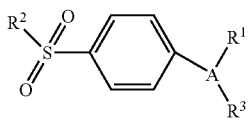

I wherein A is a 5- or 6-member ring substituent selected from partially unsaturated or unsaturated heterocyclo and carbocyclic rings;

wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl, and amino; and wherein $R^3$ is a radical selected from halo, alkyl, alkenyl, alkyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkyltrioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arysulfonyl, N-alkyl-N-arylaminosulfonyl; or a pharmaceutically-acceptable salt thereof.

The invention would be useful for, but not limited to, organ transplantation procedures and a variety of disease states. For example, combinations of the invention would be useful to treat a recipient of a graft of a transplanted organ to reduce recipient rejection of the graft or to reduce a donor leukocyte response against the recipient's tissues. Such combinations would be useful, in particular, for transplants of bone marrow, kidney, liver, heart, heart-lung and pancreas organs. Combinations of the invention would also be useful in suppressing immune response in a human or animal subject susceptible to or afflicted with an autoimmune disease or inflammatory disease. Examples of such treatable disease are graft vs. host disease, systemic lupus erythematosis, multiple sclerosis, myasthenia gravis, thyroiditis, Graves' disease, autoimmune hemolytic anemia, aplastic anemia, autoimmune thrombocytopenia purpura, mixed connective tissue disease, idiopathic Addison's disease, Sjogren's syndrome, insulin dependent diabetes mellitus, rheumatoid arthritis, osteoarthritis, skin and muco-epithelial diseases such as psoriasis (in all its forms) lichen, chronic eczema, and pityriasis, glomerulonephritis, inflammatory bowel disease, Crohn's disease, alopecia areata, pemphigus and pemphigoid, dermatomyositis, polymyositis, Behcet's disease, uveitis, pulmonary sarcocidiosis, biliary cirrhosis, and atopic dermatitis. Combinations of the invention would also be useful in suppressing immune response in a human or animal subject susceptible to or afflicted with an allergy, such as an asthmatic condition or reaction, urticaria or with airway hypersensitivity. The invention would also be useful in suppressing immune response in a human or animal subject afflicted with or susceptible to septic shock. Combinations of the invention would also be useful in preventing or suppressing acute or delayed-type hypersensitivity responses or conditions resulting from or associated with hypersensitivity responses such as contact dermatitis, hemolytic a antibody-induced thrombocytopenia, Goodpasture's syndrome, hypersensitivity, pneumonitis, glomerulonephritis, granulomas, thyroiditis, encephelomyelitis, and meningitis. The invention would also be useful in the treatment of cancer, including leukemia, lymphoma and solid tumors, including pancreatic, breast, colon, lung, epithelial and melanoma tumors.

Besides being useful for human treatment, these compounds are also useful for veterinary treatment of mammals, including companion animals and farm animals, such as, but not limited to, horses, dogs, cats, cows, sheep and pigs.

Compositions of the invention would be useful in treating organs prior to transplant. For example, an organ removed from a donor could be stored or transported in a bath containing an immunosuppressive composition of the invention. The immunosuppressive composition would act to inhibit donor leukocyte reactivity.

Compositions of the invention would also be useful in adjunct therapy involving, typically, coadministration with an additional immunosuppressive agent, such as a cyclosporin compound, or Fujisawa FK-506, or rapamycin, or a glucocorticoid, or an antiproliferative agent, or a monoclonal antibody such as an anti-CD3 (anti-T cell receptor antibody) or anti-CD5/CD7 or anti-CD4 agent, or an anti-IL-2 receptor (anti-cytokine receptor antibody) agent or an anti-IL-2 (anti-cytokine antibody), or Nippon NKT-01 (15-deoxyspergualin) or Syntex RS-61443.

The term "cyclooxygenase-2 inhibitor" embraces compounds which selectively inhibit cyclooxygenase-2 over cyclooxygenase-1. Preferably, the compounds have a cyclooxygenase-2 $IC_{50}$ of less than about 0.5 µM, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 µM, and more preferably of greater than 20 µM. Such preferred selectivity may indicate an ability to reduce the incidence of common NSAID-induced side effects.

The term "5-lipoxygenase inhibitor" embraces compounds which selectively inhibit 5-lipoxygenase with an $IC_{50}$ of less than about 10 µM. More preferably, the 5-lipoxygenase inhibitors have a 5-lipoxygenase $IC_{50}$ of less than about 1 µM.

The phrase "combination therapy" (or "co-therapy"), in defining use of a cyclooxygenase-2 inhibitor agent and a 5-lipoxygenase inhibitor agent, is intended to embrace administration of each agent in a sequential manner in a regimen that will provide beneficial effects of the drug combination. The phrase also is intended to embrace co-administration of these agents in a substantially simultaneous manner, such as in a single capsule having a fixed ratio of these active agents, or in multiple, separate capsules for each agent.

The phrase "therapeutically-effective" is intended to qualify the amount of each agent for use in the combination therapy which will achieve the goal of improvement in severity and the frequency of incidence over treatment of each agent by itself, while avoiding adverse side effects typically associated within alternative therapies.

Preferred 5-lipoxygenase inhibitors include masoprocol, tenidap, zileuton, flobufen, lonapalene, tagorizine, Abbott A-121798, Abbott A-76745, Abbott A-78773, Abbott A-79175, Abbott ABT 761, Dainippon AL-3264, Bayer Bay-x-1005, Biofor BF-389, bunaprolast, Cytomed CMI-392, Takeda CV-6504, enazadrem phosphate, Leo Denmark ETH-615, flezelastine hydrochloride, Merck Frosst L 663536, Merckle ML-3000, rilopirox, Schering Plough SCH 40120, tepoxalin, linazolast (TMK-688), Zeneca ZD-2138, Briston-Meyers Squibb BU-4601A, carbazoycin C, lagunamycin, Wellcome BW-70C, Ciba-Geigy CGS-26529, Warner-Lambert Cl 1004, Warner-Lambert PD-136005, Warner-Lambert PD-145246, Eisai E 3040, Fujirebio F-1322, Fujisawa FR 110302, Merck & Co L-699333, Merck Frosst L 739010, Lilly LY-269415, Lilly LY 178002, SmithKline Beecham SB-202235, American Home Products WAY-121520, Zeneca ZM-216800, Zeneca ZM 230487, 1,2-dihydro-n-(2-thiazolyl)-1-oxopyrrolo(3,2,1-kl)phenothiazine-1-carboxamide, Abbott A-65260, Abbott A-69412, Abbott-63162, American Home Products AHR-5333, Boehringer Ingelheim BI-L-357, Boehringer Ingelheim BI-L-93BS, Boehringer Ingelheim BIL 226XX, Bristol-Myers Squibb BMY-30094, carbazomycin B, Wellcome BW-B218C, Chauvin CBS-1114, Ciba-Geigy CGS-21595, Ciba Geigy CGS-22745, Ciba-Geigy CGS-23885, Ciba-Geigy CGS-24891, Ciba-Geigy CGS-8515, Chiese CHF-1909, Warner-Lambert CI-986, Warner-Lambert CI-987, cirsiliol, docebenone, DuPont Merck DuP-654, Eisai E 5110, Eisai E-6080, enofelast, epocarbazolin-A, eprovafen, evandamine, forsythiaside, Fisons FPL 62064, Zeneca ICI-211965, Kyowa Hakko KF-8940, Merck & Co L-651392, Merck & Co L-651896, Merck & Co L-652343, Merck & Co L-656224, Merck & Co L-670630, Merck & Co L-674636, Lilly LY-233569, Merck & Co MK-591, Merck & Co MK-886, nitrosoxacin-A, Ono ONO-5349, Ono ONO-LP-219, Ono ONO-LP-269, Warner-Lambert PD-127443, Purdue Frederick PF-5901, Sandoz QA-208-199, Rhone-Poulenc Rorer Rev-5367, Rhone-Poulenc Rorer RG-5901-A, Rhone-Poulenc Rorer RG-6966, Searle SC-41661A, Searle SC-45662, SmithKline Beecham SK&F-104351, SmithKline Beecham SK&F-104493, SmithKline Beecham SK&F-105809, Teijin TEI-8005, Terumo TMK-777, Terumo TMK-781, Terumo TMK-789, Terumo TMK-919, Terumo TMK-992, Teikoku Hormone TZI-41127, American Home Products WAY-120739, American Home Products WY 47288, American Home Products WY-48252, American Home Products Wy-50295, and Yoshitomi Y-19432.

More preferred 5-lipoxygenase inhibitors include masoprocol, tenidap, zileuton, flobufen, lonapalene, tagorizine, Abbott A-121798, Abbott A-76745, N'-[[5-(4-fluorophenoxy)furan-2-yl]-1-methyl-2-propynyl]-N'-hydroxyurea (Abbott A-78773), (R)(+)N'-[[5-(4-fluorophenoxy) furan-2-yl]-1-methyl-2-propynyl]-N-hydroxyurea (Abbott A-79175), Abbott ABT 761, Dainippon AL-3264, Bayer Bay-x-1005, Biofor BF-389, bunaprolast, Cytomed CMI-392, Takeda CV-6504, Efamol EF-40, Ciba-Geigy CGS-26529, enazadrem phosphate, Leo Denmark ETH-615, flezelastine hydrochloride, lonapalene, Merck Frosst L 663536, Merck Frosst L 699333, Merckle ML-3000, 3M Pharmaceuticals R-840, rilopirox, Schering Plough SCH 40120, tepoxalin, linazolast (TMK-688) , Tanabe T-757, Tanabe T-799, Zeneca ZD 7717, Zeneca ZM-216800, Zeneca ZM 230487, and Zeneca ZD-2138.

Even more preferred 5-lipoxygenase inhibitors include tenidap, zileuton, flobufen, lonapalene, tagorizine, Abbott A-121798, Abbott A-76745, N'-[[5-(4-fluorophenoxy)furan-2-yl]-1-methyl-2-propynyl]-N'-hydroxyurea (Abbott A-78773), (R) (+)N'-[[5-(4-fluorophenoxy)furan-2-yl]-1-methyl-2-propynyl]-N-hydroxy-urea (Abbott A-79175), Abbott ABT 761, Ciba-Geigy CGS-26529, Biofor BF-389, Cytomed CMI-392, Leo Denmark ETH-615, lonapalene, Merck Frosst L 699333, Merckle ML-3000, 3M Pharmaceuticals R-840, linazolast (TMK-688), Tanabe T-757, Tanabe T-799, Zeneca ZD 7717, Zeneca ZM-216800, Zeneca ZM 230487, and Zeneca ZD-2138.

A preferred class of compounds which inhibit cyclooxygenase-2 consists of compounds of Formula I wherein A is selected from oxazolyl, isoxazolyl, thienyl, dihydrofuryl, furyl, pyrrolyl, pyrazolyl, thiazolyl, imidazolyl, isothiazolyl, cyclopentenyl, phenyl, and pyridyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; and wherein $R^3$ is a radical selected from halo, lower alkyl, oxo, cyano, carboxyl, lower cyanoalkyl, heteroaryloxy, lower alkyloxy, lower cycloalkyl, phenyl, lower haloalkyl, 5- or 6-membered heterocyclo, lower hydroxyalkyl, lower aralkyl, acyl, phenylcarbonyl, lower alkoxyalkyl, heteroaryloxy, alkoxycarbonyl, aminocarboryl, alkylaminocarbonyl, alkylamino, aminoalkyl, alkylaminoalkyl, aryloxy, and aralkoxy; or a pharmaceutically-acceptable salt thereof.

A more preferred class of compounds which inhibit cyclooxygenase-2 consists of compounds of Formula I wherein A is selected from oxazolyl, isoxazolyl, dihydrofuryl, imidazolyl, and pyrazolyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is amino; and wherein $R^3$ is a radical selected from oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclo, lower hydroxyalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

An even more preferred class of compounds which inhibit cyclooxygenase-2 consists of compounds of Formula I wherein A is selected from oxazolyl, isoxazolyl, imidazolyl, and pyrazolyl; wherein $R^1$ is phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, cyano, carboxyl, methoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, nitro, methoxymethyl, methylsulfinyl, fluoro, chloro, bromo, methoxy, ethoxy, propoxy, n-butoxy, pentoxy, and methylthio; wherein $R^2$ is amino; and wherein $R^3$ is a radical selected from oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluoromethyl, difluoromethyl, trifluromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylinocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminonmethyl, benzyloxy, and phenyloxy; or a pharmaceutically-acceptable salt thereof.

A family of specific compounds of particular interest within Formula I consists of compounds and pharmaceutically-acceptable salts thereof as follows:

3-(3,4-difluorophenyl) -4-(4-methylsulfonylphenyl)-2-(5H) -furanone;

3-phenyl-4-4-methylsulfonylphenyl)-2-(5H)-furanone;

4-[5-(4-chlorophenyl)-3-(trifluoromethyl)-1H-pyrazol-1-yl] benzenesulfonamide;

4-[5-(4-methylphenyl)-3-(trifluoromethyl)-1H-pyrazol-1-yl]benzenesulfonamide;

4-[5-(3-fluoro-4-methoxyphenyl)   -3-(difluoromethyl)-1-pyrazol-1-yl]benzenesulfonamide;

3-[1-[4-(methylsulfonyl)phenyl]-4-trifluoromethyl-1H-imidazol-2-yl]pyridine;

2-methyl-5-[1-[4-(methylsulfonyl)phenyl]-4-trifluoromethyl-1H-imidazol-2-yl] pyridine;

4-[2-(5-methylpyridin-3-yl)-4-(trifluoromethyl)-1H-imidazol-1-yl]benzenesulfonamide;

4-[5-methyl-3-phenylisoxazol-4-yl]benzenesulfonaimine;

4-[5-hydroxyethyl-3-phenylisoxazol-4-yl]benzenesulfonamide;

[2-trifluoromethyl-5-(3,4-difluorophenyl)-4-oxazolyl]benzenesulfonamide;

4-[2-methyl-4-phenyl-5-oxazolyl]benzenesulfonamide; and oxazolyl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at lease one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having at least one carbon-carbon triple bond, and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl" and "lower alkenyl", embrace radicals having "cis" and "trans" orientations, or alternatively, "E" and "Z" orientations. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" braces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substitutes selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclo" embraces saturated, partially unsaturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclo radicals include dihydrothiophene, dihydropyran, dihydrofuran and dihydrothiazole. The term "heteroaryl" embraces unsaturated heterocyclo radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclo group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3, 4-thiadiazolyl, 1,2,5-thiadiazolyl, etc.) etc.; unsaturated condensed heterocyclo group containing 1 to 2 sulfur atoms and 1 to 3 nitrogen atoms (e.g., benzothiazolyl, benzothiadiazolyl, etc.) and the like. The term "heteroaryl" embraces radicals where heterocyclo radicals are fused with aryl radicals. Examples of such fused bicyclic radicals include benzofuran, benzothiophene, and the like. Said "heterocyclo group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as "alkylsulfonyl", denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such aryl radicals include alkanoyl and aroyl radicals. Examples of such lower alkanoyl radicals include formyl, acetyl, propionyl, butynyl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other such as "carboxyalkyl", denotes —CO$_2$H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl porions having one to six carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alyl, aryl and aralkyl radicals, as defined herein, attached to a carbonyl radical. Examples of such radicals include substituted or unsubstituted methylcarbonyl, ethylcarbonyl, phenylcarbonyl and benzylcarbonyl. The term "aralkyl" embraces arylsubstituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocycloalkyl" embraces saturated and partially unsaturated heterocyclo-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "araloxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which are substituted with one or two alkyl radicals. Preferred are "lower alkylamino" radicals having alkyl porions having one to six carbon atoms. Suitable lower alkylamino may be monosubstituted N-alkylamino or disubstituted N,N-alkylamino, such as N-methylamino, N-ethylamino, N,N-dimethylamino, N,N-diethylamino or the like. The term "arylamino" denotes amino groups which are substituted with one or two aryl radicals, such as N-phenylamino. The "arylamino" radicals may be further substituted on the aryl ring portion of the radical. The term "aralkylamino" embraces amino groups which are substituted with one or two aralkyl radicals. The terms "N-arylaminoalkyl" and "N-aryl-N-alkyl-aminoalkyl" denote aminoalkyl groups which are substituted with one aryl radical or one aryl and one alkyl radical, respectively. Examples of such radicals include N-phenylaminomethyl and N-phenyl-N-methylaminomethyl. The term "aminocarbonyl" denotes an amide group of the formula —C(=O) NH₂. The term "alkylaminocarbonyl" denotes an aminocarboryl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl" and "lower N,N-dialkylaminocarbonyl" radicals with lower alkyl portions as defined above. The term "alkylaminoalkyl" embraces radicals having one or more alkyl radicals attached to an aminoalkyl radical. The term "aryloxyalkyl", embraces radicals having an aryl radicals attached to an alkyl radical through a divalent oxygen atom. The term "arylthioalkyl" em races radicals having an aryl radicals attached to an alkyl radical through a divalent sulfur atom.

The present invention comprises a pharmaceutical composition comprising a therapeutically-effective amount of a 5-lipoxygenase inhibitor compound and a cyclooxygenase-2 inhibitor compound in association with at least one pharmaceutically-acceptable carrier, adjuvant or diluent.

The present invention also comprises a method of treating immune-associated disorders in a subject, the method comprising treating the subject having or susceptible to such disorder with a therapeutically-effective amount of a 5-lipoxygenase inhibitor and a cyclooxygenase-2 inhibitor compound. The method of the present invention also includes prophylactic treatment.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclo, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The cyclooxygenase-2 inhibitor compounds of the invention can be synthesized according to the following procedures of Schemes I-X, wherein the R¹-R³ substituents are as defined for Formula I, above, except where further noted.

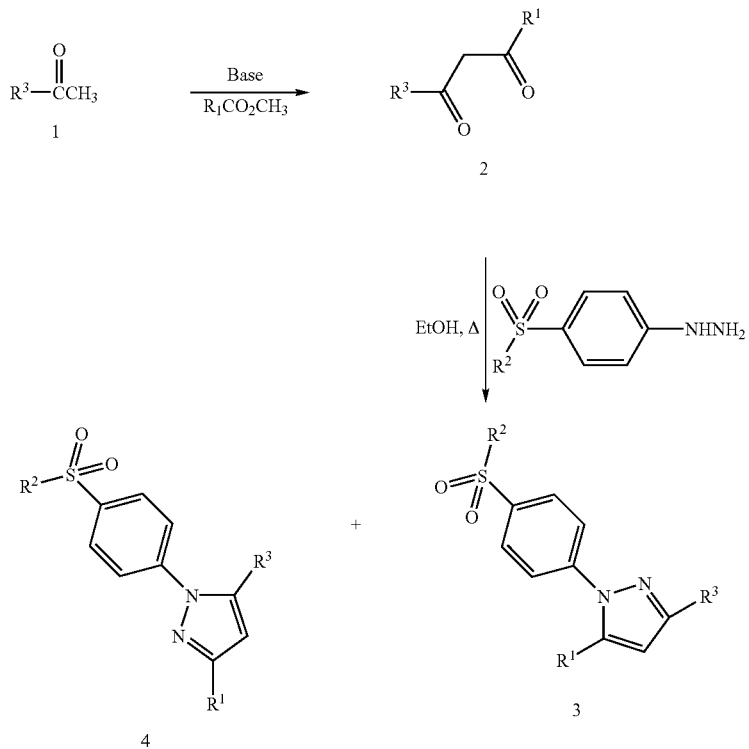

Synthetic Scheme I shows the preparation of cyclooxygenase-2 inhibitor compounds, as described in U.S. patent application Ser. No. 08/223,629, which is incorporated by reference embraced by Formula I In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochloride salt or the free base of a substituted hydrazine at reflux to afford mixture of pyrazoles 3 and 4. Recrystallization or chromatography affords 3 usually as a solid. Similar pyrazoles can be prepared by methods described in U.S. Pat. Nos. 4,146,721, 5,051,518, 5,134,142 and 4,914,121 which also are incorporated by reference.

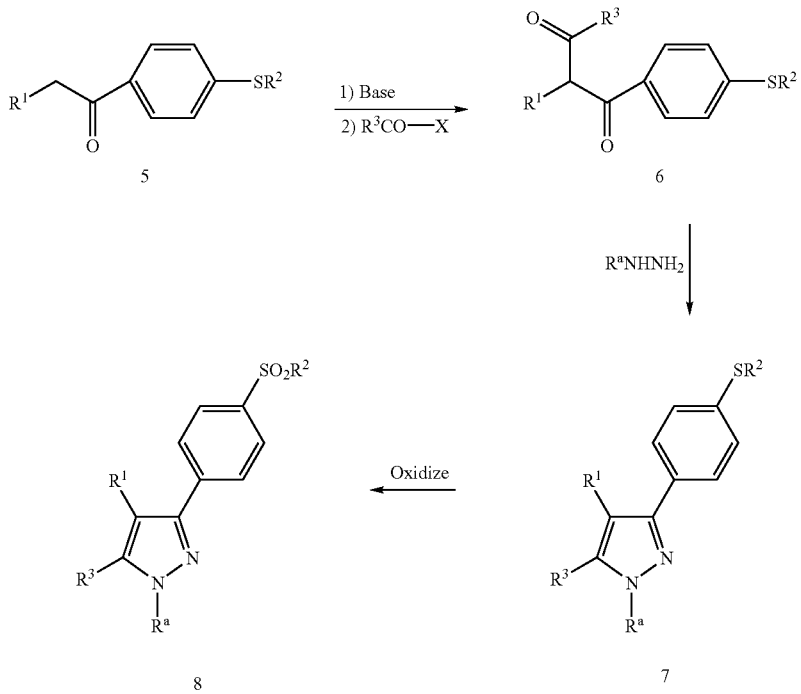

Scheme II shows the four step procedure for forming cyclooxygenase-2 inhibitor pyrazoles 8 as described in U.S. patent application Ser. No. 08/278,297 (where $R^a$ is hydrido or alkyl) from ketones 5. In step 1, ketone 5 is reacted with a base, such as lithium bis(trimethylsilyl)amide or lithium diisopropylamide (LDA) to form the anion. In step 2, the anion is reacted with an acetylating reagent to provide diketone 6. In step 3, the reaction of diketone 6 with hydrazine or a substituted hydrazine, gives pyrazole 7. In size step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer. The desired pyrazole 8, usually a white or pale yellow solid, is obtained in pure form either by chromatography or recrystallization.

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated by reference.

Scheme III
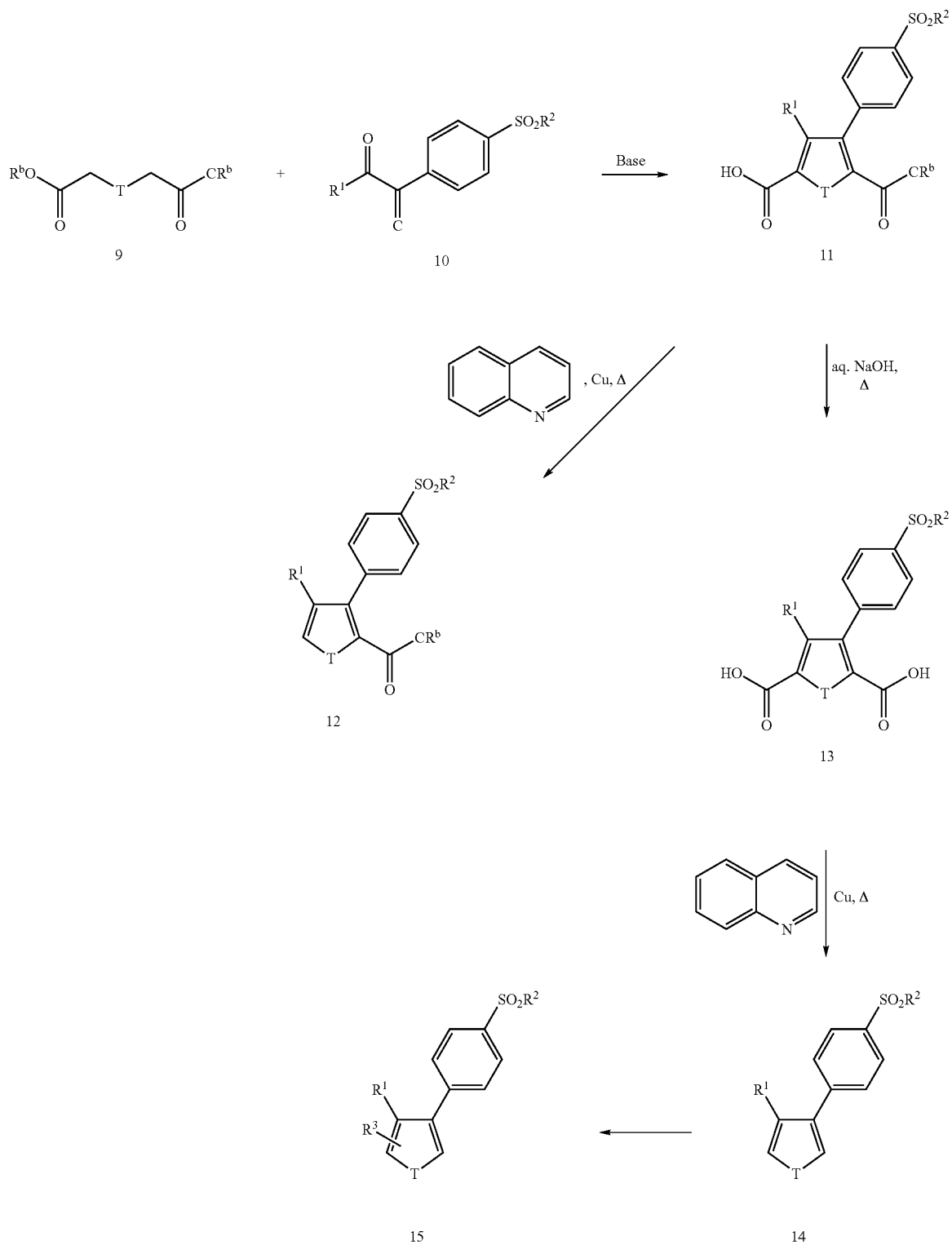
Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 05/00501 and WO94/15932.

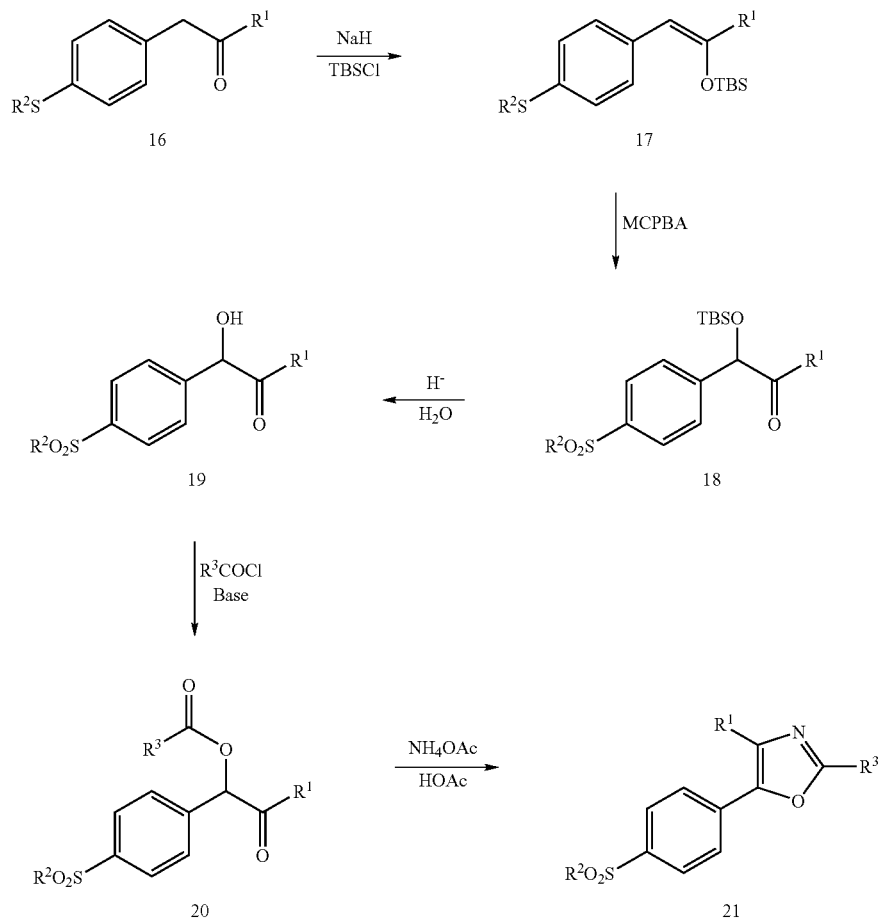

Cyclooxygenase-2 inhibitor diaryl/heteroaryl oxazoles can be prepared by the methods described in U.S. Pat. Nos. 3,743,656, 3,644,499 and 3,647,858, and PCT documents WO 95/00501 and WO94/27980, which are incorporated by reference.

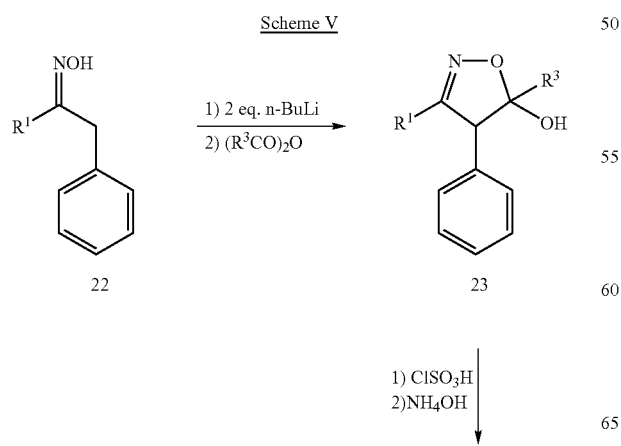

-continued

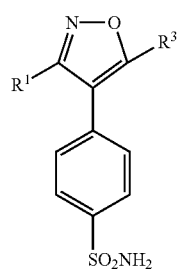

Cyclooxygenase-2 inhibitor diaryl/heteroaryl isoxazoles can be prepared by the methods described in U.S. application Ser. No. 08/387,680, PCT, documents WO92/05162, and WO92/19604, and European Publication. EP 26928 which are incorporated by reference. Sulfonamides 24 can be formed from the hydrated isoxazole 23 in a two step procedure. First, hydrated isoxazole 23 is treated at about 0° C. with two or three equivalents of chlorosulfonic acid to form the corresponding sulfonyl chloride. In step two, the sulfonyl chloride thus formed is treated with concentrated ammonia to provide the sulfonanide derivative 24.

Scheme VI

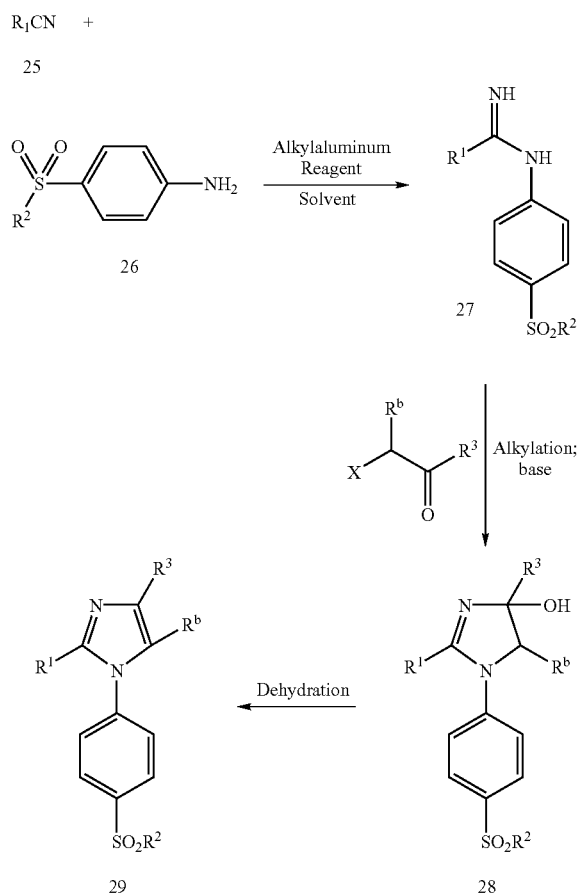

Scheme VI shows the three step preparation of the cyclooxygenase-2 inhibitor imidazoles 29 of the present invention. In step 1, the reaction of substituted nitriles ($R^1CN$) 25 with primary phenylamines 26 in the presence of alkylaluminum reagents such as trimethylaluminum, triethylaluminum, dimethylaluminum chloride, diethylaluminum chloride in the presence of inert solvents such as toluene, benzene, and xylene, gives amidines 27. In step 2, the reaction of amidine 27 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 28 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 28 may be dehydrated in the presence of an acid catalyst such as 4-toluenesulfonic acid or mineral acids to form the 1,2-disubstituted imidazoles 29 of the invention. Suitable solvents for this dehydration step are e.g., toluene, xylene and benzene. Trifluoroacetic acid can be used as solvent and catalyst for this dehydration step.

In some cases (e.g., where $R^3$=methyl or phenyl) the intermediate 28 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. Nos. 4,822,805, U.S. application Ser. No. 08/282,395 and PCT document WO 93/14082, which are incorporated by reference.

Scheme VII

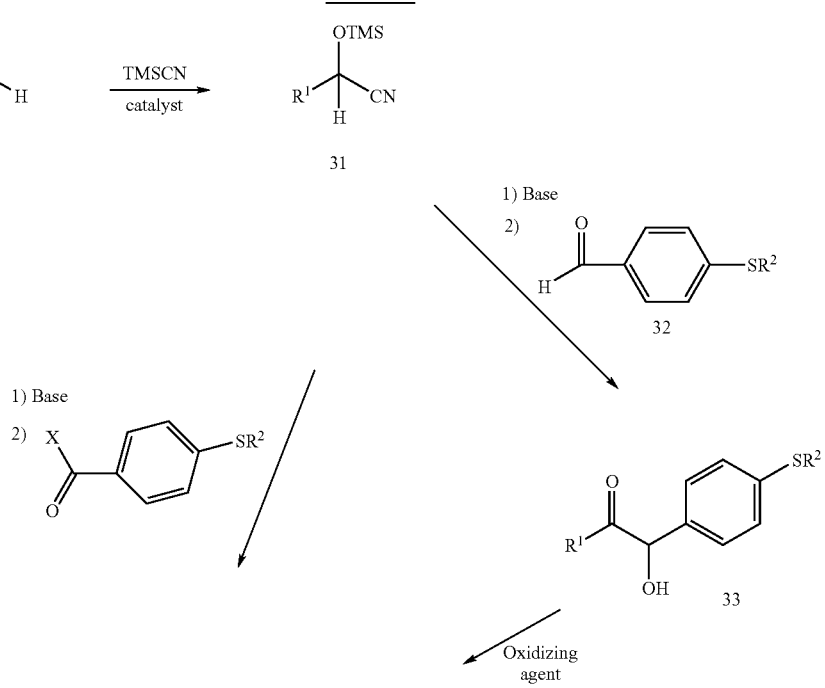

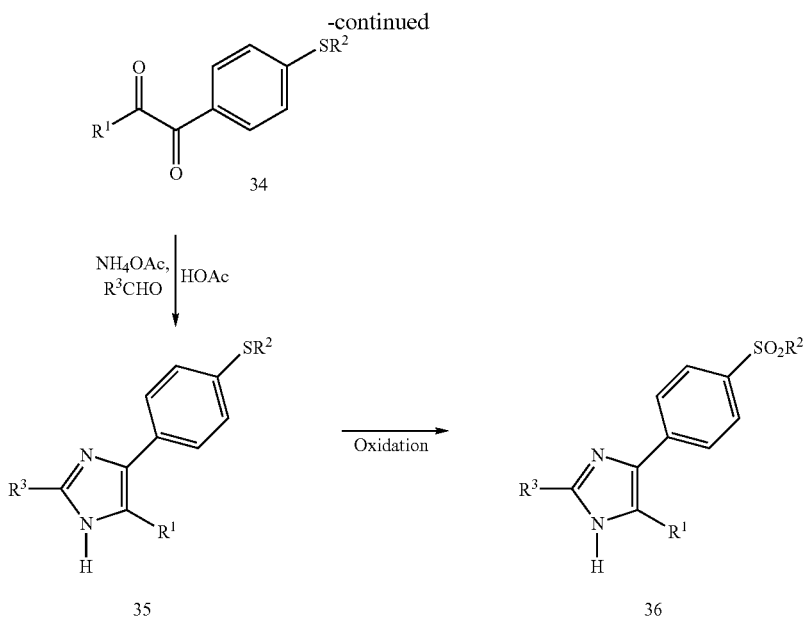

The subject imidazole cyclooxygenase-2 inhibitor compounds 36 of this invention may be synthesized according to the sequence coined in Scheme VII. Aldehyde 30 may be converted to the protected cyanohydrin 31 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 31 with a strong base followed by treatment with benzaldehyde 32 (where $R^2$ is alkyl) and using both acid and base treatments, in that order, on workup gives benzoin 33. Examples of strong bases suitable for this reaction are lithium diisopropylamide (LDA) and lithium hexamethyldisilazane. Benzoin 33 may be converted to benzil 34 by reaction with a suitable oxidizing agent, such as bismuth oxide or manganese dioxide, or by a Swern oxidation using dimethyl sulfoxide (DMSO) and trifluoroacetic anhydride. Benzil 34 may be obtained directly by reaction of the anion of cyanohydrin 31 with a substituted benzoic acid halide. Any of compounds 33 and 34 may be used as intermediates for conversion to imidazoles 35 (where $R^2$ is alkyl) according to chemical procedures known by those skilled in the art and described by M. R. Grimmett, "*Advances in Imidazole Chemistry*" in Advances in Heterocyclic Chemistry, 12, 104 (1970). The conversion of 34 to imidazoles 35 is carried out by reaction with ammonium acetate and an appropriate aldehyde ($R^3CHO$) in acetic acid. Benzoin 36 may be converted to imidazoles 38 by reaction with formamide. In addition benzoin 36 may be converted to imidazoles by first acylating with an appropriate acyl group ($R^3CO$—) and then treating with ammonium hydroxide. Those skilled in the art will recognize that the oxidation of the sulfide (where $R^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, U.S. application Ser. No. 08/281,903 European publication EP 372,445, and PCT document WO 95/00501, which are incorporated by reference.

Scheme VIII

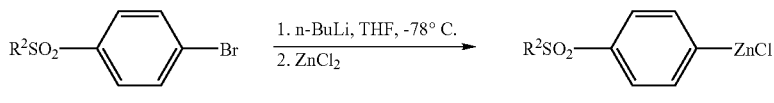

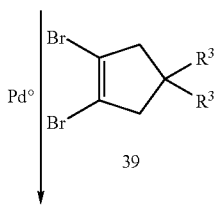

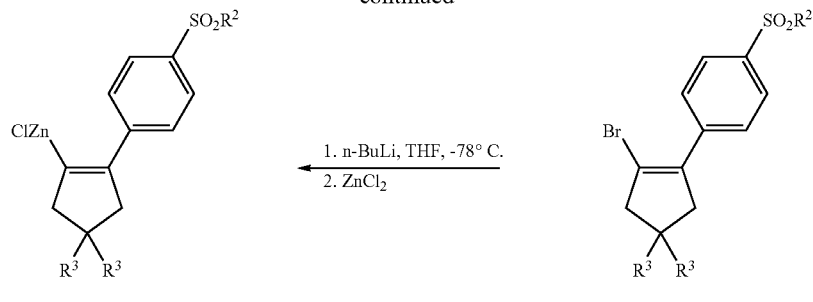

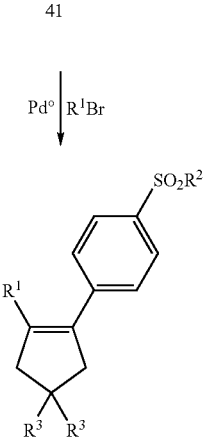

Diaryl/heteroaryl cyclopentene cyclooxygenase-2 inhibitors can be prepared by the methods described in U.S. Pat. No. 5,344,991, and PCT document WO 95/00501, which are incorporated by reference.

Scheme IX

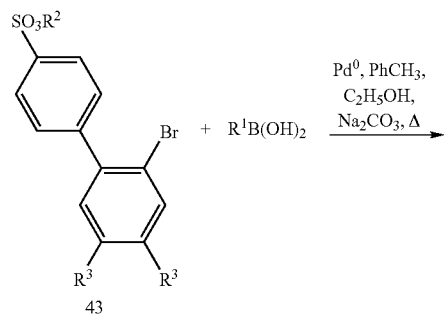

Similarly, Synthetic Scheme IX shows the procedure for the preparation of 1,2-diarylbenzene cyclooxygenase-2 inhibitor agents 44 from 2-bromo-biphenyl intermediates 43 (prepared similar to that described in Synthetic Scheme VIII) and the appropriate substituted phenylboronic acids. Using a coupling procedure similar to the one developed by Suzuki et al. [*Synth. Commun.*, 11, 513 (1981)], intermediates 43 are reacted with the boronic acids in toluene/ethanol at reflux in the presence of a Pd° catalyst, e.g., tetrakis (triphenylphosphine)palladium(0), and 2M sodium carbonate to give the corresponding 1,2-diarylbenzene antiinflammatory agents 44 of this invention. Such terphenyl compounds can be prepared by the methods described in U.S. application Ser. No. 08/346,433, which is incorporated by reference.

Scheme X

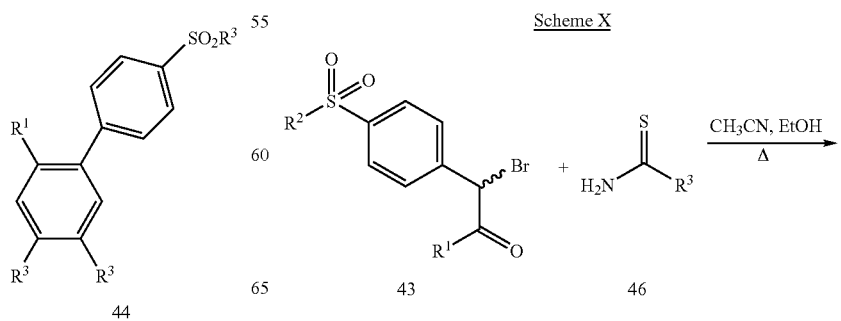

-continued

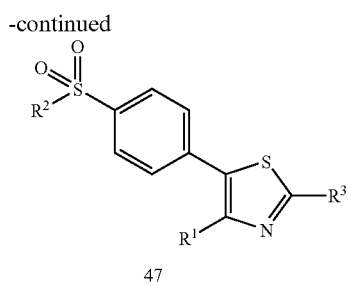

47

Diaryl/heteroaryl triazole cyclooxygenase-2 inhibitors can be prepared by the methods described in U.S. Pat. No. 4,051,250, 4,632,930, U.S. application Ser. No. 08/281,288, European Application EP 592,664, and PCT document WO 95/00501, which are incorporated by reference. Isothiazoles can be prepared as described in PCT document WO 95/00501.

Diaryl/heteroaryl pyridine cyclooxygenase-2 inhibitors can be prepared by the methods described in U.S. Pat. Nos. 5,169,857, 4,011,328, 4,533,666, U.S. application Ser. No. 08/386,843 and U.S. application Ser. No. 08/387,150 which are incorporated by reference.

The following examples contain detailed descriptions of the methods of preparation of combinations with compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NOR spectra consistent with their assigned structures.

EXAMPLE 1

4-[5-(4-Chlorophenyl)-3-(trifluoromethyl)-1H-pyrazol-1-yl]benzenesulfonamide

Step 1: Preparation of 4,4,4-trifluoro-1-[4-(chlorophenyl]-butane-1,3-dione.

Ethyl trifluoroacetate (23.52 g, 166 mmol) was dissolved in methyl tert-butyl ether (75 mL). To the stirred solution was added 25 weight % sodium methoxide (40 mL, 177 mmol). 4'-Chloroacetophenone (23.21 g, 150 mmol) was dissolved in methyl tert-butyl ether (20 mL) and added to the reaction dropwise. After stirring overnight (15.75 hours), 3N HCl (70 mL) was added. The organic layer was collected, washed with brine (75 mL), dried over MgSO$_4$, filtered, and concentrated in vacuo to give a yellow-orange solid. The solid was recrystallized from isooctane to give the dione (31.96 g, 85%): mp 66–67° C.

Step 2: Preparation of 4-[5-(4-chlorophenyl)-3-(trifluoromethyl)-1H-pyrazol-1-yl]benzenesulfonamide.

4-Sulphonamidophenyl hydrazine hydrochloride (982 mg, 4.4 mmol, 1.1 equiv.) was added to a stirred solution of 4,4,4-trifluoro-1-[4-(chloro)phenyl]-butane-1,3-dione from Step 1 (1.00 g, 4.0 mmol) in ethanol (50 mL). The reaction was heated to reflux and stirred for 20 hours. After cooling to room temperature, the reaction mixture was concentrated in vacuo. The residue was taken up in ethyl acetate and washed with water and brine. The residue was dried over MgSO$_4$, filtered, and concentrated in vacuo to give a light brown solid. The solid was recrystallized from ethyl acetate and isooctane to give the pyrazole (1.28 g, 80%): mp 143–145° C.; EI GC-MS M+=401.

EXAMPLE 2

4-[5-(3-Fluoro-4-methoxyphenyl)-3-(difluoromethyl)-1H-pyrazol-1-yl]benzenesulfonamide Step 1: Preparation of 3'-fluoro-4'-methoxy-acetophenone.

Acetyl chloride (51.0 g, 0.65 mol) was added dropwise to a stirred solution of aluminum chloride (80.0 g, 0.6 mol) and chloroform (750 mL), maintaining the temperature between 5–10° C. The mixture was stirred for 10 minutes at 5° C. before the dropwise addition of 2-fluoroanisole (62.6 g, 0.5 mol). The mixture was stirred at 0–10° C. for 1 hour and poured into ice (1 L). The resultant layers were separated and the aqueous layer was extracted with dichloromethane (2×250 mL) The combined organic layers were washed with water (2×150 mL), dried over anhydrous MgSO$_4$, filtered and concentrated in vacuo to a volume of 300 mL. Hexanes were added and a white solid formed which was isolated by filtration and air dried. This material was recrystallized from a mixture of dichloromethane and hexanes to afford material suitable for use in the next step (77.2 g, 92%): mp 92–94° C.

Step 2: Preparation of 4,4-difluoro-1-(3-fluoro-4-methoxyphenyl)-butane-1,3-dione.

Ethyl difluoroacetate (4.06 g, 32.7 mmol) was dissolved in methyl tert-butyl ether (50 mL)). To the stirred solution was adds 25 weight % sodium methoxide (7.07 g, 32.7 mmol) followed by 3'-fluoro-4'-methoxyacetophenone from Step 1 (5.0 g, 29.7 mmol). After stirring for 16 hours, 1N HCl (50 mL) was added. The organic layer was collected and washed with water (2×50 mL) , dried over anhydrous MgSO$_4$, filtered, and added to hexanes to precipitate a tan solid (7.0 g, 96%): mp 70–72° C.

Step 3: Preparation of 4-[5-(3-fluoro-4-methoxyphenyl)-3-(difluoromethyl)-1H-pyrazol-1-yl]benzenesulfonamide.

4,4-Difluoro-1-(3-fluoro-4-methoxyphenyl)-butane-1,3-dione from Step 2 (7.0 g, 28.4 mmol) was dissolved in ethanol (150 mL). To the stirred mixture was added 4-sulphonamidophenyl hydrazine hydrochloride (7.4 g, 33 mmol) and stirred at reflux overnight (16 hours). The mixture was cooled and water was added until crystals slowly appeared. The product was isolated by filtration and air dried to provide the desired product as a light tan solid (9.8 g, 87%): mp 159–161° C. Anal. Calc'd. for $C_{17}H_{14}N_3SO_3F_3$: C, 51.38; H, 3.55; N, 10.57. Found: C, 51.46; H, 3.52; N, 10.63.

EXAMPLE 3

N'-[3-[5-(4-Fluorophenoxy)furyl-2-yl]-1-methyl-2-propynyl]-N'-hydroxyurea

N-[3-[5-(4-Fluorophenoxy)furyl-2-yl]-1-methyl-2-propynyl]-N'-hydroxyurea was synthesized as described in WO document 92/01682: Anal. Calc'd. for $C_{15}H_{13}N_2O_4F$: C, 59.21, H, 4.31, N, 9.21. Found: C, 58.93, H, 4.32, N, 9.07.

BIOLOGICAL EVALUATION

The combinations of the invention were evaluated as described in the following tests.

Transplantation and Evaluation of Graft Resection

The method of skin grafting used has been previously described [D. Steinmuller, Skin Grafting. Surgical Techniques in Immunology, Methods Enzymol. 108, 20 (1984)]. Briefly, a tailskin from an 8–12 week old male B10.Br mouse was removed and stored in cold saline. Male C57BL/10 mice were anesthetized, and their backs were shaved. The backs were scrubbed with alcohol, and a 1 cm$^2$ piece of skin was removed. A similar size piece of skin was cut from the tailskin of the B10.Br mouse and placed in the excised area on the C57BL/10 animal's back. A petroleum jelly coated bandage was placed over the graft and held in place by a single surgical staple. Compounds were prepared as a suspension in 0.5% methylcellulose (Sigma, St. Louis, Mo.), and 0.025% Tween® 20 (Sigma). The compounds were administered by i.p. injection in a volume of 0.1 ml beginning on the day of skin grafting and continuing until transplant rejection. Cyclosporin A (csa) was purchased as "Sandimmune Injection" at a pharmacy. Compounds were administered alone or as combinations of a COX-2 and 5-LO inhibitor. Bandages were left in place until 8 days post grafting. At that time they were removed, and the grafts were observed daily or signs of rejection. Rejection was determined by complete blackening or scabbing of the grafted skin. Results are shown in Table 1.

TABLE 1

Skin Graft Rejection Time

| Example | Ex. #1 Rejection (days) | Ex. #2 Rejection (days) | Ex. #3 Rejection (days) | Ex. #4 Rejection (days) |
|---|---|---|---|---|
| Vehicle | 15.0 | 16.8 | 15.8 | 15.2 |
| 1 (COX – 2) | | | | |
| 2 (COX – 2) | 15.7 | | 17.3 | |
| 3 (5 – LO) | 15.0 | | 17.0 | |
| COX – 2 + LO | | | | |
| 1 + 3 | | | | 17.0 |
| 2 + 3 | | 19.2 | 18.8 | |
| csa | | | | 17.2 |
| 1 + 3 + csa | | | | 20.3 |

Dosing Ranges:
Example 1 @ M, W, F @ 10 mpk/day;
Example 2 @ 30 mpk/day, q.d.;
Example 3 @ 10 mpk/day, q.d.;
csa @ 5 mpk/day, b.d.

Thus it can be seen that treatment with either a COX-2 inhibitor or the 5-LO inhibitor alone resulted in no significant prolongation to graft survival in 2 separate experiments compared to the vehicle treated control animals. The combination of Example 2 and Example 3 showed a significant delay in rejection time in 2 experiments. Graft rejection was delayed by 2.4 and 3.0 days, respectively, as compared to vehicle. The coadministration of Example 1 and Example 3 with a low dose of the immunosuppressant cyclosporin A resulted in a significant 5.1 day prolongation of graft survival. The cyclosporin alone also did not significantly prolong graft survival. These results indicate that dual blockade of the COX-2 and 5-LO enzymes may enhance prolongation of the survival and may have additive or synergistic effects when combined with cyclosporin.

EXAMPLE 4

A formulation is prepared having the following components:
700 mg of a cyclooxygenase-2 inhibitor and 700 mg of a 5-lipoxygenase inhibitor.

EXAMPLE 5

A formulation is prepared having the following components:
350 mg of 4-[5-(3-fluoro-4-methoxyphenyl)-3-(difluoromethyl)-1H-pyrazol-1-yl]benzenesulfonamide and 700 mg of N'-[[5-(4-fluorophenoxy)furan-2-yl]-1-methyl-2-propynyl]-N'-hydroxyurea.

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose so water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.05 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For disorders of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration the active ingredient through the skin or other affected areas. Examples of such dermal penetration enhancers include dimethylsulfoxide and related analogs. The compounds of this invention can also be administered by a transdermal device. Preferably topical administration will be accomplished using a catch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxy-propylmethyl cellulose. Formulations for parenteral administration may be if he form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A pharmaceutical composition comprising a pharmaceutically-acceptable carrier and a therapeutically-effective amount of a 5lipoxygenase selective inhibitor, a cyclosporin compound and a cyclooxygenase-2 selective inhibitor selected from flosutide 5-bromo-2-(4-fluorophenyl)-3-f4-(methylsulfonyl)phenyll-thiophene, N-[2-cyclohexyloxy)-4-nitrophenyll-methanesulfonamide, 1,1-dioxide-4-hydroxy-2-methyl-N-(5-methyl-2-thiazolyl)-2H-1,2-benzothiazine-3-carboxamide, N-[6-(2,4difluorophenoxy)-2,3-dihydro-1-oxo-1 H-inden-5-yl]-methanesulfonamide and compounds of Formula I or a pharmaceutically acceptable salt of a compound having Formula I:

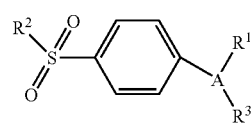

wherein A is a 5-or 6-member ring substituent selected from partially unsaturated or unsaturated heterocyclo and carbocyclic rings;

wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl, and amino; and wherein $R^3$ is a radical selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, arylaminocarbonyl, alkyl-N-arylaminocarbonyl, alkylaminocarbonylalkyl, carboxyalkyl, alkylamino, arylamino, N-aralkylamino, N-alkyl-N-arylaminocarbonyl, alkyl-N-arylamino, aminoalkyl, alkylaminoalkyl, arylaminoalkyl, N-aralkylaminoalkyl, alkyl-Naralkylaminoalkyl, alkyl-N-arylaminoalkyl, aryloxy, aralkoxy, arylthio, aralkylthio, alkylsulfinyl, alkylsulfonyl, aminosulfonyl, alkylaminosulfonyl, arylaminosulfonyl, arylsulfonyl and alkyl-N-arylaminosulfonyl.

2. A composition comprising:

a 5-lipoxygenase selective inhibitor selected from the group consisting of: (Z)-5-Chloro-2,3-dihydro-3-(hydroxy-2-thienylmethylene)-2-oxo-1H-indole-1-carboxamide, (1-Benzo[b]thien-2-yl-ethyl)-N-hydroxyurea, 4-[2',4'-difluorbiphenyl]-4-oxomethyl-butanic acid, 6-chloro-2,3-dimethoxynaphthalene-1,4-diol-diacetate, (2E)-N-[4[4-(diphenylmethyl)-1-pipe razinyl-Jbutyl]-3-(6-methyl-3-pyridinyl)-2-propenamide, 1methyl-6-[[[3-(tetrahydro-4-methoxy-2-methyl-2 H-pyran-4-yl)-2-propenyl]oxyJmethyl]2(1H)-quinolinone, Hydroxy-N-[4-[3-(4-fluorophenoxy)p hen yl]-2-propynyl]-N-hydroxyurea, [3-[5-(4-fluorophenoxy)-2-furanyl]-1-methyl-2-propynyl]-N-hydroxyurea, (R)-(+)-N-[3-[5-[(4fluorophenyl)methyl]-2-thienyl]-1-methyl-2-propynyl]-N-hydroxyurea, [2-[[2-[(4'fluoro [1,1'-biphenyl]-4-yl )methyl]-1,2,3,4-tetrahydro-1-oxo-6-isoquinolinyl]oxy]ethyl]-Nhydroxy-urea, dihydro-4-(3,5-di-tert-butyl-4-hydroxybenzylidene)-2-methyl-2H-1 ,2oxazin-3(4H )-one, 4-(2-quinolylmethoxy)-N-(3-fluorobenzyl-phenyl-amino-methyl-4benzoic-acid, 6-chloro-2,3-dimethoxynaphthalene-1, 4-diol-diacetate, (2-[2-[1-(4chlorobenzyl)-4-methyl-6-[(5-phenylpyridin-2-yl)methoxy]-4,5-dihydro-1 Hthiopyrano[2,3,4-cd]indol-2-yl]ethoxy]-butanoic acid, [2,2-dimethyl-6-(4-chlorophenyl)-7phenyl-2,3-dihydro-1 H-pyrrolizine-5-yl]-acetic acid, 1-([5-(3-methoxy-4-ethoxycarbonyloxyphenyl)-2,4-pentadienoyl]aminoethyl)-4-diphenylmethoxypiperidine, 2-[2,3-dihydro-1-methoxy-6-(2-naphthalenylmethoxy)-1 H-inden-1-yl]-thiazole, (6-[(3fluoro-5-[4-methoxy-3,4,5,6-tetrahydro-2H-pyran-4-yl])phenoxymethyl]-1-ethyl-2quinolone, and 6-[(3-fluoro-5-[4-methoxy-3,4,5,6-tetrahydro-2H-pyran-4-yl])phenoxymethyl]-1-methyl-2-quinolone;

a cyclooxygenase-2 selective inhibitor selected from the group consisting of: 3-(3,4-difluorophenyl)-4-(4-methylsulfonylphenyl)-2-(5H )-furanone; 3-phenyl-4-(4-methylsulfonylphenyl)-2-(5H)-furanone; 4-[5-(4-chlorophenyl)-3-(trifluoromethyl)-1 H-pyrazol-1-yl]benzenesulfonamide; 4-[5-(4-methylphenyl)-3-(trifluoromethyl)-1 H-pyrazol-1-yl] benzenesulfonamide; 4-[5-(3-fluoro-4-methoxyphenyl)-3-(difluoromethyl)-1 H-pyrazol-1yl]benzenesulfonamide;

3-[1-[4-(methylsulfonyl)phenyl]-4-trifluoromethyl-1 H-imidazol-2-yl]pyridine; 2-methyl-5-[1-[4-(methylsulfonyl)phenyl]-4-trifluoromethyl-1 H-imidazol-2yl]pyridine;

4-[2-(5-methylpyridin-3-yl)-4-(trifluoromethyl)-1 H imidazol-1yl]benzenesulfonamide;

4-[5-methyl-3-phenylisoxazol-4-yl]benzenesulfonamide; 4-[5-hydroxyethyl-3-phenylisoxazol-4 yl]benzenesulfonamide; [2-trifluoromethyl-5-(3,4-difluorophenyl)-4-oxazolyl]benzenesulfonamide; 4-[2-methyl-4-phenyl-5-oxazolyl]benzenesulfonamide; and 4-[5-(3-fluoro-4-methoxyphenyl-2-trifluoromethyl)-4 oxazolyl]benzenesulfonamide; and a cyclosporin compound.

3. The composition of claim 2 wherein the cyclooxygenase-2 selective inhibitor is 3-(3,4-difluorophenyl)-4-(4methylsulfonylphenyl)-2-(5H)-furanone.

4. The composition of claim 2 wherein the cyclooxygenase-2 selective inhibitor is 3-phenyl-4-(4-methylsulfonylphenyl)-2-(5H )furanone.

5. The composition of claim 2 wherein the cyclooxygenase-2 selective inhibitor is 4-[5-(4-chlorophenyl)-3-(trifluoromethyl)-1 Hpyrazol-1-yl]benzenesulfonamide.

6. The composition of claim 2 wherein the cyclooxygenase-2 selective inhibitor is 4-[5-(4-methyl phenyl)-3-(trifluoromethyl)-1 Hpyrazol-1-yl]benzenesulfonamide.

7. The composition of claim 2 wherein the cyclooxygenase-2 selective inhibitor is 4-[5-(3-fluoro-4-methoxyphenyl)-3(difluoromethyl)-1 H-pyrazol-1-yl]benzenesulfonamide.

8. The composition of claim 2 wherein the cyclooxygenase-2 selective inhibitor is 3-[1-[4-(methylsulfonyl)phenyl]-4trifluoromethyl 1 H-imidazol-2-yl]pyridine.

9. The composition of claim 2 wherein the cyclooxygenase-2 selective inhibitor is 2-methyl-5-[1-[4-(methylsulfonyl)phenyl]-4trifluoromethyl-1 H-imidazol-2-yl]pyridine.

10. The composition of claim 2 wherein the cyclooxygenase-2 selective inhibitor is 4-[2-(5-methylpyridin-3-yl)-4-(trifluoromethyl)1 H-imidazol-1-yl]benzenesulfonamide.

11. The composition of claim 2 wherein the cyclooxygenase-2 selective inhibitor is 4-[5-methyl-3-phenylisoxazol-4yl]benzenesulfonamide.

12. The composition of claim 2 wherein the cyclooxygenase-2 selective inhibitor is 4-[5-hydroxyethyl-3-phenylisoxazol-4yl]benzenesulfonamide.

13. The composition of claim 2 wherein the cyclooxygenase-2 selective inhibitor is [2-trifluoromethyl-5-(3,4-difluorophenyl)-4oxazolyl]benzenesulfonamide.

14. The composition of claim 2 wherein the cyclooxygenase-2 selective inhibitor is 4-[2-methyl-4-phenyl-5oxazolyl]benzenesulfonamide.

15. The composition of claim 2 wherein the cyclooxygenase-2 selective inhibitor is 4-[5-(3-fluoro-4-methoxyphenyl-2trifluoromethyl)-4-oxazolyl]benzenesulfonamide.

16. A composition comprising 4-[5-(4-methylpheny))-3-(trifluoromethyl)-1 H-pyrazol-1-yl]benzenesulfonamide, N'-[[5-(4fluorophenoxy)furan-2-yl]-1-methyl-2-propynyl]-N'-hydroxyurea and a cyclosporin compound.

17. A composition comprising 4-[5-(3-fluoro-4methoxyphenyl)-3-(difluoromethyl)-1 H-pyrazol-1-yl]benzenesulfonamide, N'-[[5-(4fluorophenoxy)furan-2-yl]-1-methyl-2-propynyl]-N'-hydroxyurea and a cyclosporin compound.

18. A composition comprising 4-[5-methyl-3-phenylisoxazol-4-yl]benzenesulfonamide, N'-[[5-(4-fluorophenoxy)furan-2-yl]-1-methyl2-propynyl]-N'-hydroxyurea and a cyclosporin compound.

* * * * *